United States Patent
Takahashi et al.

(10) Patent No.: US 8,567,233 B2
(45) Date of Patent: Oct. 29, 2013

(54) GAS CHARGE CONTAINER, ATOM PROBE APPARATUS, AND METHOD FOR ANALYZING HYDROGEN POSITION IN MATERIAL

(75) Inventors: Jun Takahashi, Tokyo (JP); Kazuto Kawakami, Tokyo (JP); Haruo Ohmori, Yokohama (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 502 days.

(21) Appl. No.: 12/997,480

(22) PCT Filed: Jun. 24, 2009

(86) PCT No.: PCT/JP2009/061478
§ 371 (c)(1),
(2), (4) Date: Dec. 10, 2010

(87) PCT Pub. No.: WO2009/157475
PCT Pub. Date: Dec. 30, 2009

(65) Prior Publication Data
US 2011/0113858 A1    May 19, 2011

(30) Foreign Application Priority Data

Jun. 24, 2008  (JP) ............................. P2008-164619
May 12, 2009  (JP) ............................. P2009-115426

(51) Int. Cl.
*G01N 9/00* (2006.01)

(52) U.S. Cl.
USPC .................... 73/31.05; 73/19.01; 73/25.01

(58) Field of Classification Search
USPC ................................. 73/19.01, 25.01, 31.05
See application file for complete search history.

(56) References Cited

U.S. PATENT DOCUMENTS

| 4,716,736 A | 1/1988 | Schwarz | |
|---|---|---|---|
| 2003/0152345 A1* | 8/2003 | Viswanathan et al. | ........ 385/123 |

FOREIGN PATENT DOCUMENTS

| JP | 48-56952 U | 7/1973 |
|---|---|---|
| JP | 48-100577 U | 11/1973 |
| JP | 62-216901 A | 9/1987 |
| JP | 3-101852 U | 10/1991 |
| JP | 9-152410 A | 6/1997 |
| JP | 9-196831 A | 7/1997 |
| JP | 10-104141 A | 4/1998 |
| JP | 11-30573 A | 2/1999 |
| JP | 2002-33366 A | 1/2002 |
| JP | 2003-123682 A | 4/2003 |
| SU | 1126846 A1 | 11/1984 |

OTHER PUBLICATIONS

Russian Office Action with the English translation dated Feb. 12, 2012, for Application No. 2010151790.

(Continued)

*Primary Examiner* — Hezron E Williams
*Assistant Examiner* — Rodney T Frank
(74) *Attorney, Agent, or Firm* — Birch, Stewart, Kolasch & Birch, LLP (57) ABSTRACT

A gas charge container includes a sample holder which holds a needle-shaped material, a deutrium gas supply portion which charges a deutrium gas into the needle-shaped material held by the sample holder, and a heating portion which heats the needle-shaped material held by the sample holder. The needle-shaped material is cooled by blocking the heat generated by the heating portion after the needle-shaped material is heated by the heating portion.

7 Claims, 5 Drawing Sheets

(56) References Cited

OTHER PUBLICATIONS

Notice of Allowance dated Feb. 20, 2013 issued in Korean Patent application No. 10-2010-7028276 (translation is provided).
Russian Notice of Allowance dated May 16, 2012 issued in Application No. 2010151790 (English translation is attached).
"Nanotechnology for Supporting the Advancement of Steels", Shiraishi Kinen Koza (SMS-ISIJ), 53.54.
"The Behavior of Hydrogen Charged from the Local Region (Visualization of Localized Hydrogen in Steels-2)", CAMP-ISIJ, vol. 13, (2000), pp. 1379-1381, (492-494)
International Search Report PCT/JP2009/061478 dated Sep. 15, 2009.
K. Hono, "Atom probe field Ion microscopy (APFIM, 3DAP)", Bulletin of the Iron and Steel Institute of Japan (Ferrum) 4 (1999), pp. 474-481.
Kenichi Takai et al., "Observation of Trapping Sites of Hydrogen and Deuterium in High-Strength Steels with Secondary Ion Mass Spectrometry", Journal of Japan Institute of Metals, vol. 58, No. 12 (1994), pp. 1380-1385.
Observation of Hydrogen Distribution in Tempered Martensitic Structure with Tritium Autoradiography, CAMP-ISIJ, vol. 14, (2001), pp. 645, (339).
Russian Office Action with the English translation dated Feb. 17, 2012, for Application No. 2010151790.

* cited by examiner

GAS CHARGE CONTAINER, ATOM PROBE APPARATUS, AND METHOD FOR ANALYZING HYDROGEN POSITION IN MATERIAL

BACKGROUND OF THE INVENTION

1. Field of the Invention

The present invention relates to a gas charge container, an atom probe apparatus, and a method for analyzing a hydrogen position in a material. Particularly, the present invention relates to a technique which directly measures atoms of a sample one by one, thereby improving the functions of an atom probe apparatus which can investigate the atomic structure of a very minute region. According to this technique, since the existence position of hydrogen in a material which was conventionally difficult to observe can be directly observed, the technique can greatly contribute to development of materials with excellent hydrogen embrittlement resistance.

Priority is claimed on Japanese Patent Application No. 2008-164619 filed on Jun. 24, 2008 and Japanese Patent Application No. 2009-115426 filed on May 12, 2009, the contents of which are incorporated herein by reference.

2. Description of Related Art

As introduced in Text of "Nanotechnology for Supporting the Advancement of Steels", Shiraishi Kinen Koza (SMS-ISIJ), 53•54, the Iron and Steel Institute of Japan, an atom probe apparatus can measure the space position and element species of constituent atoms of a sample with a high spatial resolution of a nanometer or less, and is used for, for example, structure analysis at the atomic level of a conductive material. The principle of the atom probe apparatus applies a high DC voltage and a high pulse voltage to a conductive sample which has been worked in the shape of a needle, carries out field evaporation of sample surface atoms sequentially by a high electric field formed on the surface of the needle, and analyzes generated ions by a detector. It is also possible to radiate a laser instead of a pulse voltage, thereby assisting in the field evaporation to analyze a nonconductive material. Since the flight time until an evaporated ion reaches the detector is determined depending on the mass of the ion, this measurement then allows the element species of the ion to be determined.

Various kinds of atom probe apparatuses have been already developed. A three-dimensional atom probe apparatus with the highest practicality can measure the arrival coordinates of an ion by a coordinates detector, thereby measuring not only the arrangement of the ion in the depth direction but an actual three-dimensional space position in the sample. Normally, a three-dimensional element position distribution in a sample can be visualized with spatial resolution at a level of lattice spacing by calculating the flight direction of an ion in consideration of the electric field distribution of a needle tip with respect to a measurement atom data set in which data on 100,000 or more atoms is collected.

Meanwhile, hydrogen in a steel material causes hydrogen embrittlement (delayed fracture or the like), and countermeasures for this have been taken for a long period of time. It is considered that the hydrogen which has entered the steel becomes a starting point (generation of a crack) of a fracture such that the hydrogen diffuses in the steel, moves and accumulates to a specific spot, and weakens the bonding force between atoms or the like. The hydrogen embrittlement is a problem in a number of metallic materials as well as steel. Although hydrogen in a steel material is a very important element in determining the reliability of the material, the hydrogen cannot be identified by direct observation. This results from a very high diffusion velocity of hydrogen, and a slight amount of solid solution. Therefore, in order to observe hydrogen in steel, conventionally, various methods or apparatuses have been developed.

Now, a method which is a most used method for investigating the amount of hydrogen which exists (trapped, dissolved, or the like) in steel is the thermal desorption method. Two kinds of methods, such as the thermal desorption—gas chromatography in argon (the thermal desorption analysis: TDA) and the thermal desorption—mass spectroscopy in vacuum (the thermal desorption spectrometry: TDS), are mainly used in this thermal desorption method. However, although the trapped energy and abundance of hydrogen can be estimated, both the methods cannot directly investigate the existence position of hydrogen.

Journal of Japan Institute of Metals, Volume 58, No. 12 (1994), and pp. 1380 to 1385 reports that hydrogen or deutrium in a steel material was observed by the secondary ion mass spectrometry (SIMS). However, the spatial resolution remains at about 2 μm. In steel materials containing a fine precipitate of 0.1 μm or less, though the fine precipitate is considered that the hydrogen trapping capacity is high, it was impossible to investigate in which portion hydrogen exists.

In the tritium radioautography described in CAMP-ISIJ, Vol. 14 (2001), and p. 645, the information on the existence position of hydrogen can be obtained, for example, by depositing silver on an emulsion applied to the surface of a steel material, or a dry plate, using radioactive rays emitted from tritium.

Additionally, in the hydrogen microprint method described in CAMP-ISIJ, Vol. 13 (2000), and pp. 1379-1381, it is possible to indirectly trap the hydrogen emitted from the surface of a steel material as a silver particle by a redox reaction with silver bromide.

However, since emulsion is used in all of them, there is no spatial resolution of 0.1 μm or less. Therefore, the determination where hydrogen exists in the steel material could not be made.

In contrast with such conventional techniques, a three-dimensional atom probe (3DAP) method has a high spatial resolution, is able to detect hydrogen in principle, and has the possibility to detect the existence position of hydrogen. Since the diffusion velocity of hydrogen is very high, a phenomenon occurs in which the hydrogen charged into a sample comes out from a trap site, and comes out from the surface of the sample only by being held at room temperature in a short time after charging. Since the sample is cooled to and measured at 100K or lower, 3DAP is advantageous in that escape of trapped hydrogen is prevented. However, even if a needle-shaped material is worked in advance and hydrogen is charged into this needle-shaped material, a phenomenon which the charged hydrogen diffuses in a short time which is taken until the needle-shaped material is introduces into the 3DAP apparatus, and escapes from the surface of the needle-shaped material occurs in a very short time. Therefore, analysis was difficult.

An apparatus and measuring method which detect a material defect on a sub-nanometer scale (to 0.2 nm) are disclosed in Japanese Unexamined Patent Application, First Publication No. H9-152410. In this method, the deutrium gas is introduced into an analysis container (analysis chamber) using the 3DAP method, deutrium is charged into a heated needle-shaped material (sample), and the resulting material is analyzed by an atom probe. The reason why the deutrium gas is used is that remaining hydrogen gas exists even within the container (chamber) which has been highly evacuated, and this remaining hydrogen gas will be post-ionized and detected, thereby hindering the distinction from the hydrogen which exists within the sample. However, even if the deutrium gas is used, since the deutrium gas is put into the container before analysis, the deutrium will remain even if evacuation is made, and completely the same phenomenon as hydrogen occurs, i.e., the remaining deutrium will be detected by post-ionization. As a result, the distinction from the deutrium charged into the sample will be hindered. Moreover, a low temperature of 100K or lower is normally required for atom probe measurement. In an ordinary apparatus, however, a long period of time of 20 minutes or more is required until the sample is cooled to this temperature. Hence, since the deutrium charged until the cooling escaped from the sample, observation of the existence position of hydrogen to be targeted was difficult.

In consideration of such a situation, a new apparatus and method which measures the existence position of hydrogen in a material at an atomic level are demanded.

SUMMARY OF THE INVENTION

In order to prevent the charged deutrium from escaping out of a sample, and to prevent contamination of the sample, in atom probe measurement, it is necessary to charge the deutrium gas within the apparatus and to suppress the escape of the charged deutrium from the sample after charging it as much as possible.

Thus, the present invention performs functional improvements to an atom probe apparatus which measures the existence positions of hydrogen in a material at an atomic level and which efficiently employs this in material design. That is, the object of the present invention is to provide a gas charge container, an atom probe apparatus, and a method for analyzing a hydrogen position in a material as those which contributes to the measurement of the existence positions of hydrogen in a material.

The present inventors have keenly studied an apparatus and method for measuring the hydrogen charged into a material with a position resolution at an atomic level. As a result, in order to avoid corrosion or change of properties of a needle-shaped material which occurs due to cathodic charge in a solution, it is considered that gas charging is preferable. As the kind of gas, it is considered that a hydrogen isotope is preferable, and deutrium gas is used. Thus, an apparatus and method for charging deutrium gas within the atom probe apparatus is suggested. Moreover, in order to prevent the charged deutrium from escaping into the needle-shaped material, an apparatus and method for rapidly cooling the charged needle-shaped material is suggested. Moreover, an apparatus and method for moving the needle-shaped material containing the charged deutrium in a low-temperature state without contaminating the sample to an analysis container in a short time are suggested. The existence positions of the hydrogen in the needle-shaped material can be observed with a spatial resolution at an atomic level by the combination of these apparatuses and optimal methods for use.

In consideration of the above, the present invention has adopted the following.

(1) A gas charge container of the present invention includes a sample holder which holds a needle-shaped material, a deutrium gas supply portion which charges a deutrium gas into the needle-shaped material held by the sample holder, and a heating portion which heats the needle-shaped material held by the sample holder, wherein the needle-shaped material is cooled by blocking a heat generated by the heating portion after the needle-shaped material is heated by the heating portion.

(2) In the gas charge container described the above (1), a configuration may be adopted in which the needle-shaped material is cooled by keeping away the heating portion from the sample holder after the needle-shaped material is heated by the heating portion.

(3) In the gas charge container described in the above (1), a configuration may be adopted in which the heating portion is an optical heating portion, and the needle-shaped material is cooled by stopping the optical heating portion after the needle-shaped material is heated by the optical heating portion.

(4) In the gas charge container described in the above (1), a configuration may be adopted in which the needle-shaped material held by the sample holder is cooled to −50° C. or lower within 10 seconds from a temperature after the heating by the heating portion.

(5) Additionally, an atom probe apparatus of the present invention includes the gas charge container described in the above (1), an analysis container which performs atom probe measurement of the needle-shaped material held by the sample holder, and a conveyance portion which conveys the sample holder from the gas charge container to an analysis position within the analysis container.

(6) Additionally, an atom probe apparatus of the present invention includes the gas charge container described in the above (1), an analysis container which performs atom probe measurement of the needle-shaped material held by the sample holder, and a valve which connects the gas charge container and the analysis container together.

(7) Additionally, in the present invention, a method for analyzing a hydrogen position in a material using an atom probe apparatus includes steps of cooling the sample holder holding the needle-shaped material as the sample to −100° C. or lower in an atmosphere including the deutrium gas supplied from the deutrium gas supply portion within the gas charge container described above (1), heating the needle-shaped material to a temperature of 100° C. or higher and maintaining the needle-shaped material at the temperature by the heating portion, cooling the needle-shaped material to −50° C. or lower within 10 seconds by the cooling portion, conveying the sample holder in a vacuum atmosphere from an inside of the gas charge container to the analysis container using the conveyance portion in a state where the needle-shaped material is kept at −50° C. or lower after the inside of the gas charge container is evacuated, and installing the sample holder at an analysis position within the analysis container, and performing atom probe measurement of deutrium in the needle-shaped material.

According to the present invention, deutrium can be simply and certainly charged into a material, and the atom probe measurement can be rapidly performed while suppressing diffusion of deutrium into the material. Therefore, functional improvements of the atom probe apparatus which can investigate a material from the composition of elements can be realized, and the hydrogen existence positions in materials including steel materials can be made clear. Hence, the apparatus and method which greatly contribute to development of materials of which the reliability is secured can be provided.

LIST OF REFERENCE SIGN

101: ANALYSIS CONTAINER (ANALYSIS CHAMBER)
102: SAMPLE STORAGE CONTAINER (SAMPLE STORAGE CHAMBER)
103: GAS CHARGE CONTAINER
104: SAMPLE INTRODUCTION CONTAINER
105: VALVE
106: REFLECTRON (ENERGY COMPENSATOR)
107: POSITION SENSITIVE DETECTOR
108: FIM SCREEN
109: NEEDLE-SHAPED MATERIAL
110: ION FLIGHT TRAJECTORY
111: TRANSFER ROD
112: FIM SCREEN WITH PROBE HOLE
113: MIRROR
114: ION DETECTOR
115: NEEDLE-SHAPED MATERIAL HEATER
116: DEUTRIUM GAS INTRODUCTION LINE
117: EVACUATION LINE
118: SAMPLE HOLDER
119: COLD FINGER
120: LIQUID NITROGEN CONTAINER
121: REFRIGERATOR (CRYOSTAT)
122: YAG LASER (LASER OSCILLATOR)
123: LENS
124: FLANGE WITH GLASS WINDOW
125: LASER OPTICAL PATH
126: PRESSURE METER

DETAILED DESCRIPTION OF THE INVENTION

Hereinafter, preferred embodiments of the present invention will be described in detail with reference to the accompanying drawings. In addition, in the present specification and drawings, duplicate description is omitted by giving the same reference numerals to constituent elements having substantially the same functional configurations.

One of fundamental embodiments of the present invention includes a gas charge container which has at least a sample holder which holds a needle-shaped material, a deutrium gas supply portion, a heating portion for heating the needle-shaped material, and a cooling portion for cooling the sample holder.

Additionally, other one of the fundamental embodiments of the present invention includes an atom probe apparatus which has at least an analysis container which performs an atom probe measurement, the gas charge container, and a portion for conveying a sample holder to an analysis position within the analysis container from the gas charge container.

Moreover, still other one of the fundamental embodiments of the present invention is a method of analyzing a hydrogen position using the atom probe apparatus. In the method of analyzing a hydrogen position, the temperature of the needle-shaped material is raised to 100° C. or higher by the heating portion, and is maintained in a state where the sample holder holding the needle-shaped material is cooled to −100° C. or lower by the cooling portion in an atmosphere including the deutrium gas supplied from the deutrium gas supply portion within the gas charge container. Thereafter, the needle-shaped material is rapidly cooled to −50° C. or lower within 10 seconds, and the inside of the gas charge container is evacuated. Then, the sample holder is conveyed in the vacuum atmosphere to the analysis container from the inside of the gas charge container, using a conveyance portion, in a state the needle-shaped material is kept at −50° C. or lower. Then, after the sample holder is installed at a predetermined analysis position within the analysis container, the atom probe measurement of deutrium in the material is performed.

Figure 1:
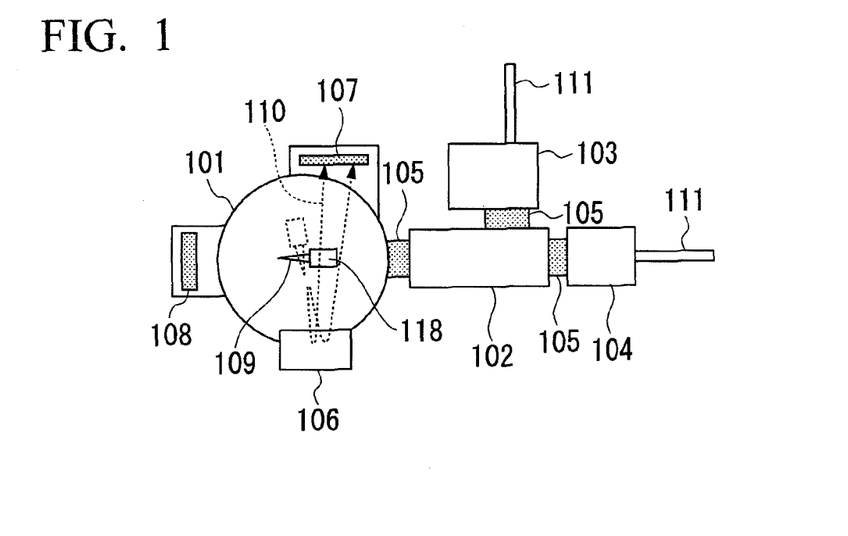
FIG. 1 is a view showing the configuration of a three-dimensional atom probe apparatus according to an embodiment of the present invention.
Figure 2:
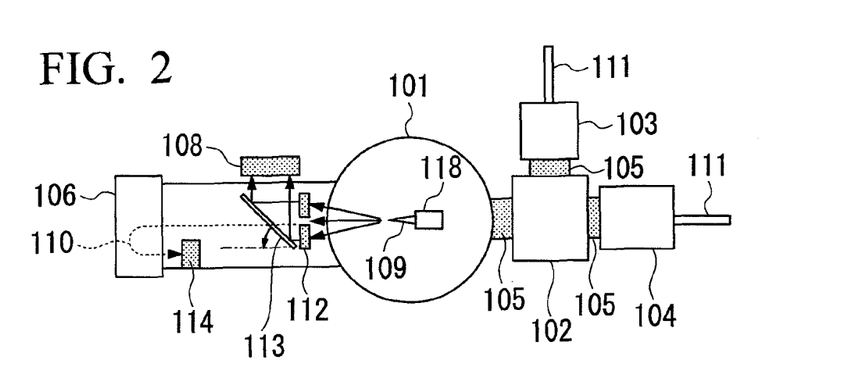
FIG. 2 is a view showing the configuration of a one-dimensional atom probe apparatus according to an embodiment of the present invention.
Figure 3:
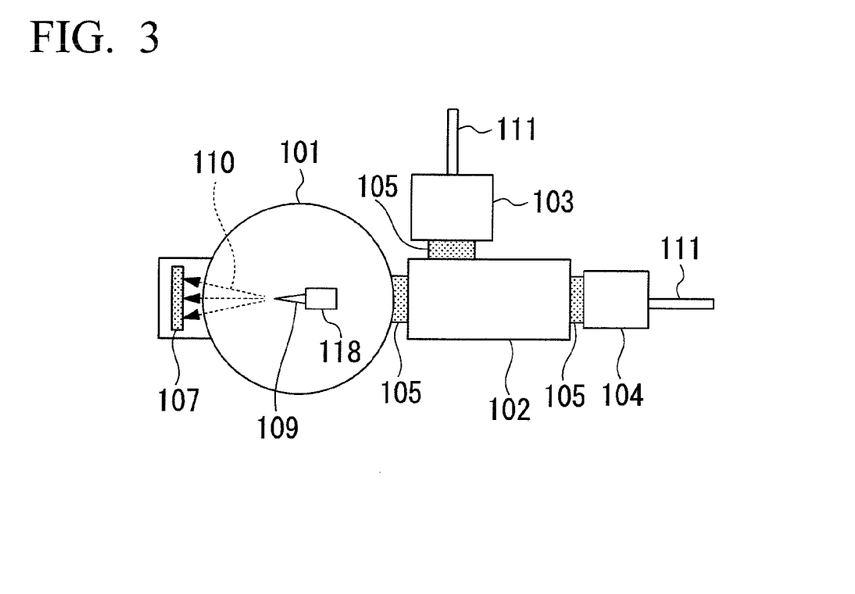
FIG. 3 is a view showing the configuration of another three-dimensional atom probe apparatus according to an embodiment of the present invention.
Figure 4:
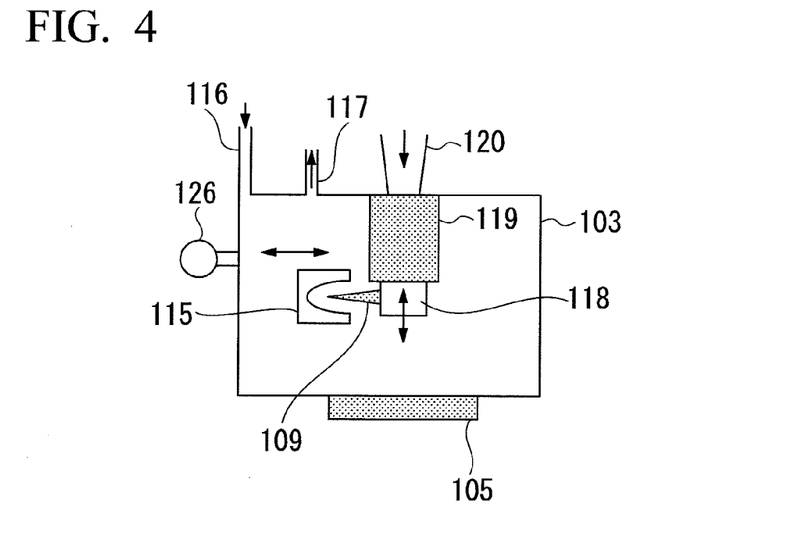
FIG. 4 is a view showing a configuration within a gas charge container according to an embodiment of the present invention.
Figure 5:
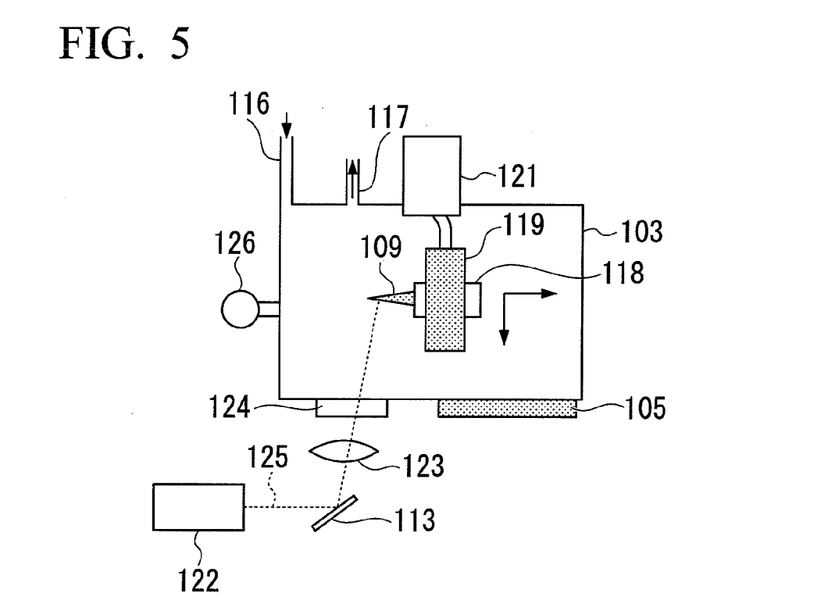
FIG. 5 is a view showing a configuration within a gas charge container according to an embodiment of the present invention.

An example of the atom probe apparatus which determines a hydrogen existence position in a material of the present invention is shown in FIGS. 1 to 3. Additionally, an example of the configuration of the gas charge container is shown in FIGS. 4 and 5. The atom probe apparatus of this embodiment has at least a portion for introducing deutrium gas within the gas charge container which is separate from the analysis container, a portion for heating the needle-shaped material, a portion for cooling the needle-shaped material rapidly, and a portion for conveying the needle-shaped material in a cooled state from the gas charge container to the analysis container.

FIG. 1 is a view showing the configuration of a three-dimensional atom probe apparatus according to an embodiment of the present invention. The three-dimensional atom probe apparatus has at least an analysis container 101; a gas charge container 103 having at least a deutrium gas introduction portion, a needle-shaped material heating portion, and a portion for rapidly cooling the needle-shaped material 109; and a conveyance portion 111 which conveys the needle-shaped material 109 to the analysis container 101. In addition, reference numeral 108 in FIG. 1 designates an FIM screen.

Additionally, FIG. 2 is a view showing the configuration of a one-dimensional atom probe apparatus according to an embodiment of the present invention. The one-dimensional atom probe apparatus has at least an analysis container 101; a gas charge container 103 having at least a deutrium gas introduction portion, a needle-shaped material heating portion, and a portion for rapidly cooling the needle-shaped material 109; and a conveyance portion 111 which conveys the needle-shaped material 109 to the analysis container 101. In addition, reference numeral 112 in FIG. 2 designates an FIM screen with a probe hole.

Additionally, FIG. 3 is a view showing the configuration of another three-dimensional atom probe apparatus according to an embodiment of the present invention. The three-dimensional atom probe apparatus has at least an analysis container 101; a gas charge container 103 having at least a deutrium gas introduction portion, a needle-shaped material heating portion, and a portion for rapidly cooling the needle-shaped material 109; and a conveyance portion 111 which conveys the needle-shaped material 109 to the analysis container 101. The three-dimensional atom probe apparatus shown in FIG. 3 is different from the three-dimensional atom probe apparatus shown in FIG. 1 in that the reflectron 106 which performs mass correction is not annexed.

A needle-shaped material 109 is manufactured outside the apparatus by electropolishing or the like, and is introduced into a sample introduction container 104 in the state of being attached to a sample holder 118. Then, after the inside of the sample introduction container 104 and the inside of the sample storage container 102 are evacuated, the material is transferred into and kept in the sample storage container 102 by a transfer rod 111.

Then, the needle-shaped material 109 can be further transferred into the gas charge container 103 from the sample storage container 102 by the transfer rod 111. In this gas charge container 103, gas can be charged under predetermined conditions to perform cooling. Moreover, the needle-shaped material 109 can be transferred to a predetermined position within the analysis container 101 through the sample storage container 102. A valve 105 is provided between respective containers to evacuate the inside of each container individually.

The needle-shaped material 109 and the sample holder 118 are arranged at predetermined positions within the analysis container 101, the needle-shaped material 109 is cooled, the inside of the analysis container 101 is maintained at a high vacuum, and a high voltage is applied to the needle-shaped material 109. As a result, surface constituent atoms of the needle-shaped material 109 can be individually ionized through field evaporation. Normally, the ionization can be performed with high controllability by superimposing a positive pulse voltage on a positive DC voltage. Additionally, the ionization can be performed with high controllability even by applying a positive DC voltage to the needle-shaped sample, and applying a negative pulse to a ring-shaped counter electrode provided at the tip of the needle-shaped sample. In the three-dimensional atom probe, the flight time of ions which have flown and the position of a detector surface can be measured. Additionally, in the one-dimensional atom probe, it is possible to measure the flight time. The flight trajectories 110 of ions are shown in FIGS. 1 to 3. In the atom probe apparatus of FIGS. 1 and 2, in order to improve mass resolution, flying ions are trapped by a detector via the reflectron 106, whereas the flying ions are directly detected by the atom probe apparatus of FIG. 3.

Figure 8:
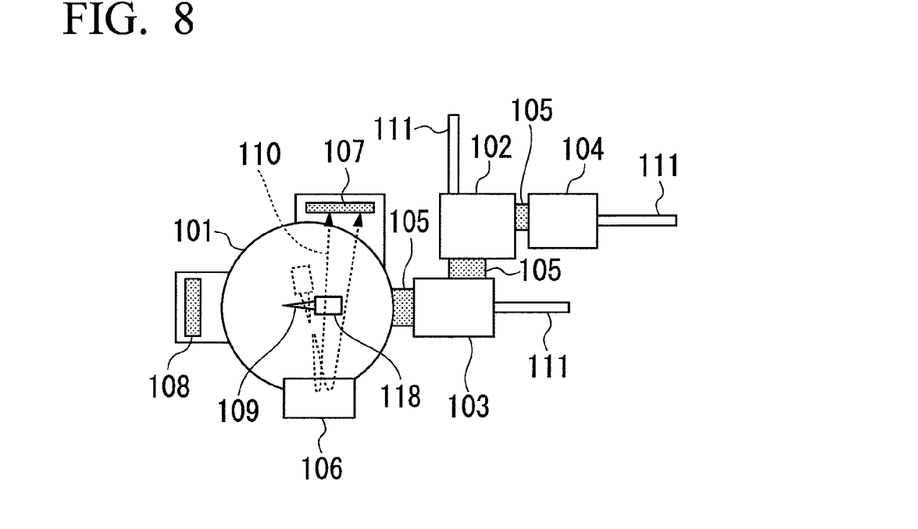
FIG. 8 shows an example of a configuration view of a more preferable atom probe apparatus according to an embodiment of present the invention.

Moreover, FIG. 8 shows a more preferable atom probe apparatus for measuring a hydrogen existence position in the needle-shaped material 109. The atom probe apparatus of this embodiment has within the gas charge container 103 which is different from the analysis container 101 at least a portion for introducing deutrium gas, a portion for heating the needle-shaped material 109, a portion for rapidly cooling the needle-shaped material 109, and a portion for conveying the needle-shaped material 109 in a cooled state from the gas charge container 103 to the analysis container 101. In addition, in FIG. 8, reference numeral 107 designates a position sensitive detector, and reference numeral 108 designates a FIM screen.

In the atom probe apparatus shown in FIG. 8, the gas charge container 103 is arranged next to the analysis container 101 via the valve 105, unlike the one shown in FIGS. 1 to 3. Therefore, after the deutrium is charged into the needle-shaped material 109 within the gas charge container 103, it is possible to rapidly convey the needle-shaped material 109 to the analysis container 101 by the transfer rod 111 connected to the gas charge container 103, and to cool the needle-shaped material 109. In the atom probe apparatus shown in FIGS. 1 to 3, after the needle-shaped material 109 is once transferred to the sample storage container 102 from the gas charge container 103, the needle-shaped material 109 is introduced into the analysis container 101. On the other hand, in the atom probe apparatus of FIG. 8, the time consumed for the transfer of the needle-shaped material 109 becomes short as much as this path is omitted, and the charged deutrium can be kept from deviating from the needle-shaped material 109. In addition, normally, although the atom probe apparatus is not used only for hydrogen analysis, in a configuration as shown in FIG. 8, this is not suitable for analysis other than the hydrogen analysis. Accordingly, the idea of making the configuration of atom probe apparatus into the configuration as shown in FIG. 8 can not be normally considered.

Figure 9:
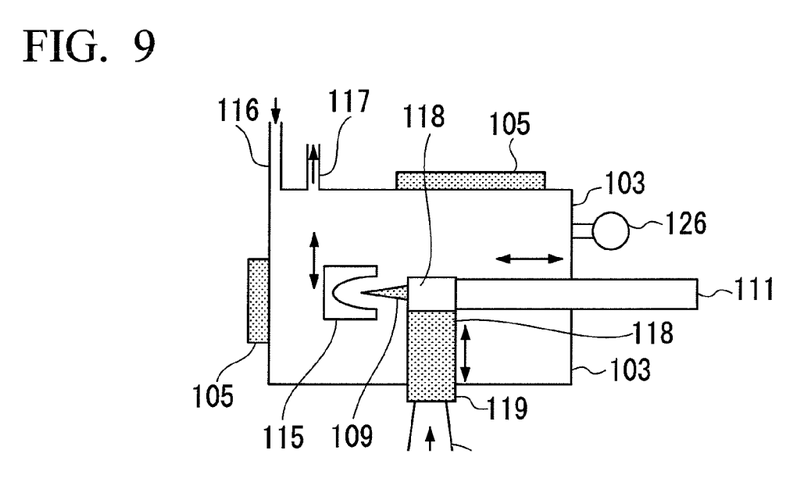
FIG. 9 is an example of a configuration view of a gas charge container according to an embodiment of the present invention.

FIGS. 4 and 5 are views showing the details within the gas charge container 103 shown in FIGS. 1 to 3. Additionally, FIG. 9 is a view showing the details within the gas charge container 103 shown in FIG. 8.

In addition, the atom probe apparatus to be described here includes a one-dimensional atom probe apparatus, a three-dimensional atom probe apparatus, and a scanning atom probe apparatus, and is an element position analysis apparatus having the spatial resolution at a level of atomic spacing.

Hereinafter, the details of the respective configurations will be described.

In order to charge deutrium into the needle-shaped material 109 which is an object to be measured, it is necessary to introduce the deutrium gas into the gas charge container 103 which stores the needle-shaped material 109 which is an object to be measured, to increase gas pressure, and to raise the temperature of the needle-shaped material 109. The shape of the needle-shaped material 109 is needle-shaped in order to allow the atom probe analysis. The gas charge container 103 which perform the charging of the deutrium gas needs to be separated from the analysis container 101 which actually performs atom probe analysis. This is because, in a conventional atom probe apparatus which performs charge and measurement of the deutrium within the same container, the distinction between the deutrium within the charged sample (needle-shaped material 109), and the deutrium detected as the remaining deutrium gas within the container is (chemically) adsorbed and ionized (post-ionized) on the sample surface, becomes difficult during atom probe measurement. The reason why gas is used for deutrium charge is that handling of introduction/evacuation or the like is easy, and corrosion or contamination of the sample surface during charging can be suppressed.

Gas pressure is applied in order to increase the frequency (number of times of trial) of the collision of the deutrium molecules with the sample (needle-shaped material 109), and to enhance the probability of entering the sample. Additionally, the temperature of the sample is raised in order to increase the energy of the deutrium molecules which collide against each other, thereby enhancing the probability of getting over a surface barrier. The deutrium partial pressure within the gas charge container 103 is preferably set to be equal to or more than 10 Torr ($1.33 \times 10^3$ Pa), and more preferably set to be equal to or more than 200 Torr ($2.67 \times 10^4$ Pa). Although the upper limit of the deutrium partial pressure within the gas charge container 103 is not particularly specified, in the case of a usual vacuum container, 1500 Torr ($2.00 \times 10^5$ Pa) becomes a limit from the view point of pressure strength. A higher pressure may be used, using a special pressure container.

The sample temperature is preferably 100° C. or higher, and more preferably 200° C. or higher. Meanwhile, if the sample temperature is too high, there is a possibility that the structure of the sample may change. Although the upper limit temperature for avoiding this varies depending on materials of the sample, the temperature is normally about 400° C. Additionally, the holding time is the time taken for sufficiently charging the deutrium into the needle-shaped material 109. Although the holding time varies depending on temperature, pressure, and materials, a range of 1 minute to 20 minutes is preferable. If the holding time is within 1 minute, a sufficient quantity of the deutrium is not charged, and if the holding time exceeds 20 minutes, the surface shape of the sample may change by effects, such as etching by the deutrium.

The deutrium gas is introduced after the gas charge container 103 is evacuated to preferably $1\times10^{-7}$ Torr ($1.3\times10^{-5}$ Pa) or lower. The introducing pressure of the deutrium gas in that case can be measured by, for example, a pressure meter attached to the gas charge container 103. The purpose of using an isotope (here, deutrium) of hydrogen is in order to allow the distinction from ions of remaining hydrogen gas which exists within the analysis container 101. Therefore, it is necessary to particularly set the partial pressure of hydrogen in the atmosphere gas pressure of the gas charge container 103 to 5% or less and more preferably 1% or less. Although other kinds of gases may exist somewhat if the deutrium gas charge is not hindered, in order to prevent the influence on the sample surface, and improve the efficiency of the deutrium gas charge, the partial pressure of the deutrium in an atmosphere gas pressure may be 90% or more, and more preferably may be 98% or more.

As a needle-shaped material heating portion for heating and maintaining the needle-shaped material 109 at a predetermined temperature, any arbitrary technique may be adopted to heat the needle-shaped material 109. For example, an electric heater is preferable which has the shape of covering the needle-shaped material 109 installed within the gas charge container 103, and can change the distance from the needle-shaped material 109. The reason why the shape of covering the needle-shaped material 109 is preferable is that only the tip portion of the needle-shaped material 109 can be effectively heated. Additionally, as other heating portion, for example, heating of the needle-shaped material 109 is also possible even by irradiating the needle-shaped material 109 within the gas charge container 103 with a laser or lamp installed to the outside of the gas charge container 103 through a flange with a glass window.

It is difficult to directly measure the temperature of the needle-shaped material 109 during charging the deutrium or cooling. Thus, for example, a thermocouple which resembles the actual needle-shaped material 109 is fabricated, and is attached to the sample holder 118 so as to measure a temperature change in advance. Then, the relationship between the output of a heater, elapsed time, or atmosphere pressure and temperature can be investigated to predict an actual temperature. Additionally, the predictive accuracy of the actual temperature can also be enhanced by installing the thermocouple at a position slightly apart from the needle-shaped material 109, and measuring this temperature during charging or cooling.

The function of rapidly cooling the needle-shaped material 109 after being heated is very important. Although the temperature of the needle-shaped material 109 is raised in a deutrium gas atmosphere to charge (absorb) the deutrium into the needle-shaped material 109, if the cooling rate during the subsequent cooling is slow, the deutrium in a trap site such as a defect, comes out from the trap site, and escapes from the needle-shaped material 109. Moreover, one which is dissolved into a matrix also escapes from the needle-shaped material 109 due to the fall of a solubility limit. Accordingly, it is necessary to cool the needle-shaped material 109 charged with the deutrium at high temperature to a low temperature in a short time. However, it is not easy to give this function within an apparatus which maintains a high degree of vacuum.

As the cooling portion for rapidly cooling the needle-shaped material 109, for example, introduction of liquid nitrogen from the liquid nitrogen container attached to the outside of the gas charge container 103, a refrigerator (cryostat) 121, or the like is preferable. It is possible to perform thermal contact to the needle-shaped material 109 through a cold finger, thereby cooling the needle-shaped material 109. However, since it is difficult to lower the sample temperature in a short time in case of normal use, for example, the following method is preferable.

That is, the sample holder 118 of the needle-shaped material 109 is brought into heat contact with the liquid nitrogen container or the refrigerator 121 in advance, and the sample holder 118 is cooled preferably to −100° C. or lower, and more preferably −150° C. or lower by the cooling portion in an atmosphere including the deutrium gas. Then, in this state, only the tip portion of the needle-shaped material 109 is heated by the heating portion, and is raised to and held at a predetermined temperature. Thereafter, the needle-shaped material 109 can be rapidly cooled to −50° C. or lower, and preferably 100° C. or lower within 10 seconds by the heat conduction from the sample holder 118, by separating the heater from the needle-shaped material 109 or by stopping the laser.

It is preferable that the time taken for cooling be shorter. Within an actual apparatus, it is not easy to cool the heated needle-shaped material 109 instantaneously. If the cooling time is substantially within 10 seconds, the charged deutrium can be observed. Additionally, it is preferable that the cooling achieving temperature at this time be lower in order not to make the charged deutrium escape out of the needle-shaped material 109 as much as possible. However, if the time taken for cooling is lengthened, the frequency of the escape of the charged deutrium increases by that much. Therefore, it is preferable that the time required for this is set to less than or equal to 1 minute.

The conveyance portion for conveying the cooled needle-shaped material 109 is one for transferring the needle-shaped material 109 charged with the deutrium from the gas charge container 103 to the analysis container 101 along with the sample holder 118. It is necessary to perform the conveyance by this conveyance portion within a time during which the temperature of the cooled needle-shaped material 109 does not rise so that the charged deutrium does not escape from the surface of the needle-shaped material 109, and so that contaminant does not adhere to the surface of the needle-shaped material 109. For example, by providing an external thread in the sample holder 118, preparing an internal thread in a transfer jig of the same size as the external thread, and screwing the external thread into the internal thread, it is possible to make a transfer in a short time. The time taken for transfer to the analysis container 101 after the cooling of the sample holder 118 is preferably within 3 minutes, and more preferably 1 minute from the viewpoint of a rise in sample temperature, and contaminant on the sample surface. Additionally, as the transfer portion, there is, for example, a transfer rod.

In order to keep contaminant from adhering to the surface of the needle-shaped material 109 during transfer, in a state before transfer, it is preferable that the degree of vacuum within the gas charge container 103 be set to $1\times10^{-7}$ Torr ($1.3\times10^{-5}$ Pa) or lower, the degree of vacuum within the sample storage container 102 be set to $1\times10^{-8}$ Torr ($1.3\times10^{-6}$ Pa) or lower, and the degree of vacuum within the analysis container 101 be set to $2\times10^{-10}$ Torr ($2.6\times10^{-8}$ Pa) or lower. If these degrees of vacuum are bad, a contaminant adheres to the surface of the needle-shaped material 109, it is necessary to remove this contaminant when the atom probe measurement is performed. This causes destruction of the needle-shaped material 109 or occurrence of noise. As a result, it becomes difficult to detect the charged deutrium.

Within the vacuumed gas analysis container 101, the atom probe apparatus cools the needle-shaped material 109 to 100K (−173° C.) or less, and more preferably 60K (−213° C.) or lower, applies a high voltage to the needle-shaped material 109, field-ionizes atoms on the surface of the needle-shaped material 109 by a high electric field formed at the tip portion of the needle, and measures the ions accelerated by a surface electric field by the detector. Only flight time is measured in the one-dimensional atom probe, and flight time and ion arrival position are measured as coordinates in the three-dimensional atom probe and the scanning atom probe.

Since the flight time is determined by the mass-to-charge ratio of ions, all element species contained in a material can be determined. The depth position can be determined in order of arrival of atoms, and the evaporation position of the needle-shaped material 109 can be determined from arrival coordinates on the detector. Targeted three-dimensional elemental maps can be obtained by measuring a number of ions of 100,000 atoms or more, and carrying out calculation processing by a computer, using, for example, three-dimensional construction software, such as POSAP or WAS. This method is described in detail in, for example, a reference of "Bulletin of The Iron and Steel Institute of Japan (Ferrum) 4 (1999), and pp. 474-481".

FIG. 9 is a schematic view showing the internal structure of the gas charge container 103 of the atom probe apparatus of FIG. 8. This gas charge container 103 is able to cool the needle-shaped material 109 by evacuating the inside thereof in high vacuum, and bringing the cold finger 119 cooled by charging the liquid nitrogen container 120 with liquid nitrogen by contact with the sample holder 118. In this state, the deutrium gas is introduced into the gas charge container 103, the heating heater 115 is brought close to the needle-shaped material 109, and the tip of the needle-shaped material 109 is locally heated. This allows the deutrium to be efficiently charged into the needle-shaped material 109. The needle-shaped material 109 can be cooled by keeping away the heating heater 115. Moreover, immediately after the inside of the gas charge container 103 is evacuated, the valve 105 of the gas analysis container (analysis chamber) 101 is opened, and the needle-shaped material 109 is transferred to a fixed position of the needle-shaped material 109 within the gas analysis container 101 which has been cooled in advance (refer to FIG. 8).

Since the atmosphere in the gas analysis container 101 has large heat capacity, the needle-shaped material 109 is immediately cooled. In addition, a method of heating the needle-shaped material 109 within the gas charge container 103 is not particularly limited, and a heater method or a laser method may be adopted. Additionally, a method of cooling the needle-shaped material 109 within the gas analysis container 101 is not particularly limited.

In the present invention, the deutrium gas which is one of hydrogen isotopes is used as the charge gas. This is because the hydrogen gas exists even if high-vacuum evacuation is made, and distinction becomes difficult due to ionization of the remaining hydrogen gas which exists within the analysis container 101. Since the isotopic ratio of the deutrium in nature is as small as 1/6600 compared with hydrogen, distinction from deutrium charged into a material is easy. Although the mass of the deutrium is twice the mass of hydrogen, since deutrium has no big difference in chemical characteristics or physical characteristics, and shows almost the same behavior as hydrogen, deutrium is effective as a substitution of a hydrogen existence position. Accordingly, as the atmosphere to be introduced into the gas charge container 103, it is preferable that the ratio of the deutrium in the atmosphere be higher. However, a kind of gas may exist somewhat as long as the gas does not affect the needle-shaped material 109.

Meanwhile, since tritium which is another one of hydrogen isotopes is a radioactive element, handling thereof is difficult. However, tritium shall be included in the present invention since the use thereof is possible if tritium is within a controlled area. That is, "deutrium" in the present invention also includes tritium.

As a material for the sample holder 118 which fixes the needle-shaped material 109, stainless steel, copper, and the like which have electrical conductivity and thermal conductivity are preferable. Additionally, a thread for attaching the sample holder to the transferring jig may be formed at the periphery of the sample holder 118. Since the needle-shaped material 109 used for the atom probe measurement has a length of about 5 mm to 12 mm, and a diameter of 1 mm or less, the needle-shaped material 109 can be fixed, for example, by putting the material into a metallic pipe made of copper, nickel, or the like with a diameter of 1 to 2 mm, and crimping this metallic pipe. Then, the needle-shaped material 109 can be fixed to the sample holder 118 by inserting this metallic pipe into the sample holder 118.

Additionally, materials to be analyzed in the present invention are metallic materials which cause a problem of hydrogen embrittlement, such as steel and aluminum.

The needle-shaped material 109 is normally manufactured using electropolishing. For example, a material to be analyzed can be worked into a rod-like shape of 0.3×0.3×10 mm, and this can be worked into a needle-shaped material 109 in which the radius of curvature of the needle tip is 100 nm or less by electropolishing, using an electrolyte which is appropriate for the material. For example, when the object to be analyzed is a steel material, a voltage of 5 V to 20 V can be applied to the material side and worked, using a mixed solution of perchloric acid and acetic acid, and a mixed solution of perchloric acid and alcohol. Additionally, a focused ion beam (FIB) can be used for milling.

After the needle-shaped material 109 fabricated by such a method is cleaned with alcohol or the like, the needle-shaped material is fixed to the sample holder 118 by the above-described method, and is introduced into the apparatus of the present invention. Normally, after the inside of the sample introduction container 104 is sufficiently evacuated, the needle-shaped material 109 is transferred to the gas charge container 103 by the transfer rod 111 or the like. The deutrium is charged into the needle-shaped material 109 by introducing the deutrium gas into the gas charge container 103, and raising the temperature of the tip portion of the needle-shaped material 109. Thereafter, the deutrium is enclosed by rapidly cooling the needle-shaped material 109. Then, with the needle-shaped material 109 cooled, the needle-shaped material 109 is transferred to the analysis container 101, and atom probe analysis is performed at a predetermined temperature. A deutrium position can be visualized with a spatial resolution of an atomic spacing by three-dimensionally mapping analysis results by exclusive software.

EXAMPLES

Hereinafter, examples using the apparatus of the present invention and the conventional apparatus will be explained.

Example 1

In order to investigate the temperature of the needle-shaped material 109 during the deutrium charge, a sample holder 118 for measurement resembling a needle-shaped material 109 was prepared in accordance with the actual needle-shaped material 109 and the sample holder 118 using the gas charge container 103 shown in FIG. 4 so that the tip of a thermocouple was located at a position 10 mm apart from the sample holder 118, and temperature measurement was performed. The inside of the gas charge container 103 shown in FIG. 4 was evacuated to $2 \times 10^{-8}$ Torr ($2.6 \times 10^{-6}$ Pa) from an evacuation line 117 by a pump.

Figure 6:
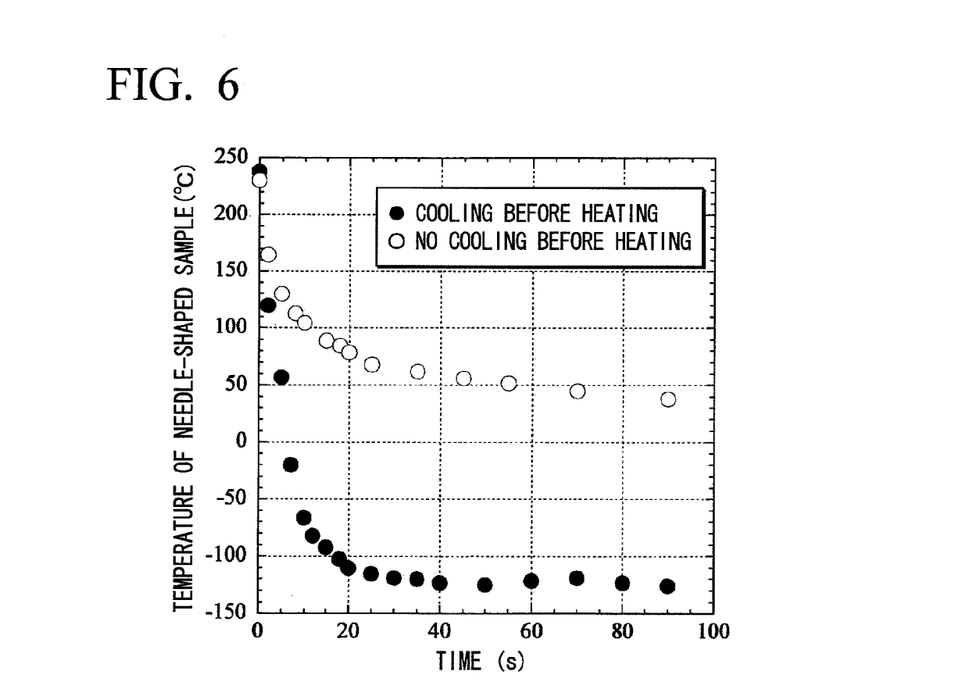
FIG. 6 is a graph showing a temperature profile of a needle-shaped material.

In this state, liquid nitrogen was poured into a liquid nitrogen container 120, and the cold finger 119, and the sample holder 118 and the needle-shaped material 109 which were brought into contact with the cold finger were cooled. The temperature of the needle tip of the needle-shaped material 109 became $-115°$ C. about 40 minutes after the start of the cooling. The deutrium gas was introduced from a deutrium gas introduction line 116 so as to have 300 Torr ($3.99 \times 10^4$ Pa), and the needle-shaped material heater 115 was brought close to the needle-shaped material 109 so as to cover the needle-shaped material 109. The needle-shaped material heater 115 was heated to raise the temperature of the needle tip of the needle-shaped material 109 in 3 minutes to about $230°$ C., and was held at this temperature for 10 minutes. While the needle-shaped material heater 115 was turned off, the needle-shaped material heater 115 was pulled apart from the needle-shaped material 109, and a temperature change was investigated. The results are shown by a closed circle in FIG. 6. The temperature of the needle tip of the needle-shaped material 109 rapidly dropped from $230°$ C. to $-70°$ C. within 10 seconds. This is considered that the needle tip was rapidly cooled due to the heat conduction to the sample holder 118 with large heat capacity since only the needle tip of the needle-shaped material 109 was heated in a state where the sample holder 118 and the cold finger 119 were sufficiently cooled. Rapid cooling within the gas charge container 103 became possible by this method. Since a portion to be heated was only the needle tip of the needle-shaped material 109, there was almost no change in atmosphere gas pressure. Additionally, although the temperature change of the needle tip during transfer was also investigated using the sample holder 118 for this measurement, the rise in temperature was lower than $20°$ C. since the sample storage container 102 through which the needle-shaped material 109 goes is maintained at a high degree of vacuum of $1 \times 10^{-8}$ Torr ($1.3 \times 10^{-6}$ Pa) and transferred within 1 minute. On the basis of such an experiment, the actual temperature of the needle tip could be estimated from the output, time, and the like of the needle-shaped material heater 115. In addition, the pressure within the gas charge container 103 was measured by a pressure meter 126, and was controlled by the valve 105. This is also the same in the following examples and comparative examples.

Comparative Example 1

Similarly to Example 1, in order to investigate the temperature of the needle-shaped material 109 during the deutrium charge, a sample holder 118 for measurement having the tip of a thermocouple arranged at a position 10 mm apart from the sample holder 118 and resembling an actual needle-shaped material 109 was prepared in accordance with the actual needle-shaped material 109 and the sample holder 118 using the gas charge container 103 shown in FIG. 4, and temperature measurement was performed.

The inside of the gas charge container 103 shown in FIG. 4 was evacuated from an evacuation line 117 by a pump. The deutrium gas was introduced from a deutrium gas introduction line 116 so as to have a pressure of 290 Torr ($3.86 \times 10^4$ Pa) without cooling the sample holder 118, and the needle-shaped material heater 115 was brought close to the needle-shaped material 109 so as to cover the needle-shaped material 109. The needle-shaped material heater 115 was heated to raise the temperature of the needle tip in 3 minutes to about $220°$ C., and was held at this temperature. While the needle-shaped material heater 115 was turned off, the needle-shaped material heater 115 was pulled apart from the needle-shaped material 109. Moreover, liquid nitrogen was poured into a liquid nitrogen container 120, and the cold finger 119, and the sample holder 118 and the needle-shaped material 109 which were brought into contact with the cold finger 119 were cooled, and the temperature change of the needle tip was investigated. The results are shown by an open circle in FIG. 6. Although the temperature of the needle tip rapidly dropped from $230°$ C. to $150°$ C., the subsequent temperature drop was very slow, and was about $50°$ C. even if 1 minute elapsed.

Example 2

A needle-shaped material 109 made of a drawn pearlite steel wire worked with the radius of curvature of the needle tip being 50 nm was attached to the sample holder 118 as shown in FIG. 4, and was introduced into the sample introduction container 104 used in Example 1. Then, the sample holder 118 was transferred into the gas charge container 103 shown in FIG. 4 along with the needle-shaped material 109, using the transfer rod 111, and the needle-shaped material heater 115 was arranged near the needle-shaped material 109.

The inside of the gas charge container 103 was evacuated to a high vacuum of $2 \times 10^{-8}$ Torr ($2.6 \times 10^{-6}$ Pa) by an evacuation line 117. Thereafter, the cold finger 119 of the liquid nitrogen container 120 into which liquid nitrogen was introduced was brought into close contact with the sample holder 118, and the sample holder 118 was cooled to $-180°$ C. In this state, the deutrium was charged into the needle-shaped material 109 by introducing the deutrium gas from the deutrium gas introduction line 116 until the pressure thereof reached a pressure of 200 Torr ($2.66 \times 10^4$ Pa), raising the temperature of the needle tip of the needle-shaped material 109 at $210°$ C. by a needle-shaped material heater 115 in the shape of covering the needle-shaped material 109, and holding the temperature for 5 minutes. After an elapse of 5 minutes, the needle-shaped material heater 115 is turned off, and separated from the position of the needle-shaped material 109, and the temperature of the needle tip of the needle-shaped material 109 was rapidly cooled to $-100°$ C. in 10 seconds.

Figure 7:
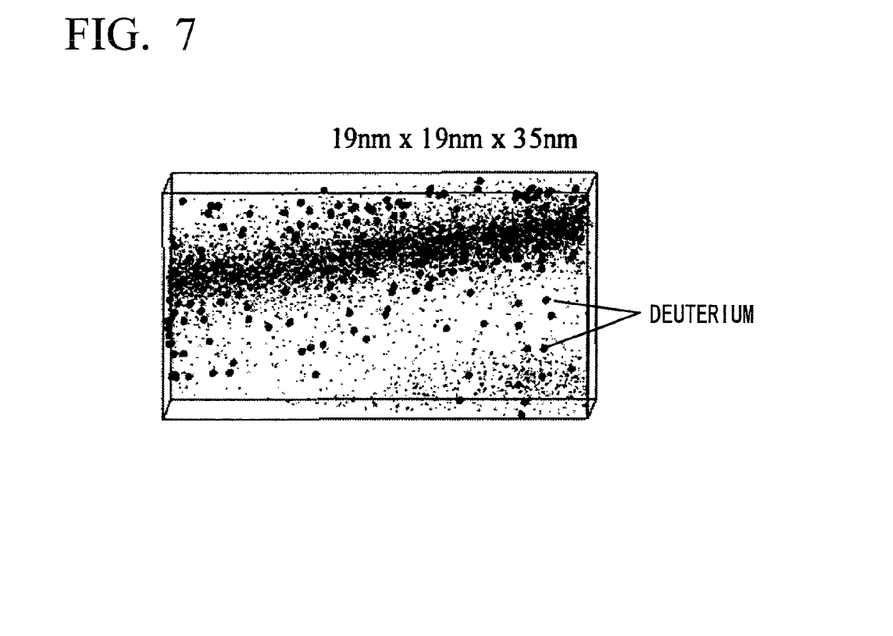
FIG. 7 is a 3DAP map (in the drawing, a small round point shows a carbon atom position, and a large round point shows a deutrium atom position) of deutrium in a drawn pearlite steel wire measured in Example 2.

In this low-temperature state, the deutrium gas was evacuated to $2 \times 10^{-8}$ Torr ($2.6 \times 10^{-6}$ Pa). Then, the needle-shaped material 109 was transferred into the gas analysis container 101 via the sample storage container 102 which was highly evacuated to $5 \times 10^{-9}$ Torr ($6.5 \times 10^{-7}$ Pa) or lower from the gas charge container 103 by the transfer rod 111. The temperature of the needle-shaped material 109 during transfer was maintained at $-70°$ C. or lower. Since a position to be analyzed within the analysis container 101 was kept at $-220°$ C. by the refrigerator 121 in advance, the temperature of the needle-shaped material 109 reached $-220°$ C. in 3 minutes. A high voltage was applied to the needle-shaped material 109 so as to cause field evaporation on the surface of the needle tip of the needle-shaped material 109, and the atom probe measurement was performed using the apparatus shown in FIG. 1. Measuring conditions are a pulse fraction of 20%, an applied voltage of DC 10 kV to 12 kV, and a pulse voltage of 2 kV to 2.4 kV. Measurement data was analyzed by POSAP software, and a mass-to-charge ratio spectrum was obtained. Hydrogen ions ($H^+$) by the ionization of remaining hydrogens within the analysis container 101 appeared as the peak of a mass-to-charge ratio of 1, whereas the peak of the charged deutrium of the deutrium ions ($D^+$) appeared in a mass-to-charge ratio of 2. The results obtained by drawing a three-dimensional elemental map on the basis of this are shown in FIG. 7. The deutrium atoms charged into pearlite steel which was subjected to wire-drawing were observed near the interface position of a cementite lamella (in FIG. 7, a small round point shows a carbon atom position, and a large round point shows a deutrium atom position), and the hydrogen existence position in the needle-shaped material 109 can be visualized and observed with spatial resolution at an atomic level.

Example 3

A needle-shaped material 109 made of precipitate-dispersed steel worked with the radius of curvature of the needle tip being 60 nm was attached to the sample holder 118, and was introduced into the sample introduction container 104 of the apparatus of the present invention. Then, the needle-shaped material 109 was arranged in a heating position of the needle-shaped material 109 by transferring the sample holder 118 into the gas charge container 103 shown in FIG. 5 along with the needle-shaped material 109, using the transfer rod 111.

After the inside of the gas charge container 103 was evacuated to a high vacuum by the evacuation line 117, the sample holder 118 was screwed into the cold finger 119 which was cooled by operating the refrigerator 121, and the sample holder 118 was cooled to −200° C.

In this state, the deutrium was charged into the needle-shaped material 109 by introducing the deutrium gas to 600 Torr ($7.98 \times 10^4$ Pa) from the deutrium gas introduction line 116, starting a continuous oscillation YAG laser 122 placed outside the gas charge container 103, taking laser light 125 into the gas charge container 103 via a mirror 113, a lens 123, and a flange 124 with a glass window, irradiating the needle tip of the needle-shaped material 109, raising the temperature of this needle tip to 180° C., and holding the temperature for 20 minutes. The achieving temperature, as described in Example 1, was investigated in advance using the sample holder with a thermocouple for measurement, and deduced from the relationship between laser output and time. After an elapse of 20 minutes, the YAG laser 122 is stopped, and the needle-shaped material 109 was rapidly cooled to the temperature of −150° C. in 10 seconds.

In this low-temperature state, the deutrium gas within the gas charge container 103 was evacuated, and the needle-shaped material 109 was transferred to the gas analysis container 101 via the sample storage container 102 from the gas charge container 103 by the transfer rod 111. The temperature of the needle-shaped material 109 during transfer was maintained at −100° C. or lower. Since an analysis position within the analysis container 101 was kept at −220° C. by the refrigerator 121 in advance, the temperature of the needle-shaped material 109 reached −220° C. in 3 minutes. A high voltage was applied to the needle-shaped material 109 so as to cause field evaporation on the surface of the needle tip of the needle-shaped material 109, and the atom probe measurement was performed.

Measuring conditions are a pulse fraction of 20%, an applied voltage of DC 12 kV to 14 kV, and a pulse voltage of 2.4 kV to 2.8 kV. Measurement data was analyzed by POSAP software, and a mass-to-charge ratio spectrum was obtained. In the mass-to-charge ratio of 2, the peak of the charged deutrium of $D^+$ appeared clearly. By investigating this distribution position, the result that the deutrium was concentrated near the interface of a precipitate was visualized.

Comparative Example 2

A needle-shaped material 109 made of a drawn pearlite steel wire worked with the radius of curvature of the needle tip being 46 nm was attached to the sample holder, and was attached to a measurement position within the gas analysis container of the atom probe apparatus resembling the apparatus described in the above Japanese Unexamined Patent Application, First Publication No. H9-152410.

After the inside of the gas analysis container was evacuated to a high vacuum by the evacuation line, the temperature of the needle-shaped material 109 was raised to 200° C. by the heating heater. In this state, the deutrium was charged into the needle-shaped material 109 by introducing the deutrium gas from a gas line until the pressure of the deutrium gas reached a pressure of 300 Torr ($3.99 \times 10^4$ Pa) and then maintaining the pressure for 10 minutes.

In this state, the needle-shaped material 109 was cooled by stopping the heating heater and operating the refrigerator 121. Simultaneously with this, the deutrium gas within the gas analysis container was evacuated. The temperature of the needle-shaped material 109 reached −220° C. in 40 minutes. Additionally, the remaining gas pressure within the gas analysis container at that time was $3 \times 10^{-10}$ Torr ($3.99 \times 10^{-8}$ Pa).

In this state, a high voltage was applied to the needle-shaped material 109 so as to cause field evaporation on the surface of the needle tip of the needle-shaped material 109, and the atom probe measurement was performed. Measuring conditions are a pulse fraction of 20%, an applied voltage of DC 9 kV to 12 kV, and a pulse voltage of 1.8 kV to 2.4 kV. Measurement data was analyzed by POSAP software, and a mass-to-charge ratio spectrum was obtained. Although the peak of the mass-to-charge ratio of 2 corresponding to the deutrium ions was measured, since the deutrium was evenly detected in the needle-shaped material 109, it was estimated that the deutrium which existed in the remaining gas and which was adsorbed on the surface of the needle-shaped material 109 was measured regarding to much of the peak. As a result, in the apparatus according to this Comparative Example 2, it was difficult to investigate the deutrium position in a targeted material.

Example 4

A needle-shaped material 109 made of precipitate-dispersed steel worked with the radius of curvature of the needle tip being 50 nm was attached to the sample holder 118 shown in FIG. 8, and was introduced into the sample introduction container 104. Then, the sample holder 118 was transferred into the gas charge container 103 shown in FIGS. 8 and 9 along with the needle-shaped material 109, using the transfer rod 111, and the needle-shaped material heater 115 was arranged near the needle-shaped material 109.

The inside of the gas charge container 103 was evacuated to a high vacuum of $2 \times 10^{-8}$ Torr ($2.6 \times 10^{-6}$ Pa) via the evacuation line 117. Thereafter, the cold finger 119 of the liquid nitrogen container 120 into which liquid nitrogen was introduced was brought into close contact with the sample holder 118, and the sample holder 118 was cooled to −180° C.

In this state, the deutrium was charged into the needle-shaped material 109 by introducing the deutrium gas into the gas charge container 103 from the deutrium gas introduction line 116 until the pressure thereof reached a pressure of 300 Torr ($4.0 \times 10^4$ Pa), raising the temperature of the needle-shaped material 109 at 180° C. by the needle-shaped material heater 115 in the shape of covering the needle-shaped material 109, and holding the temperature for 10 minutes. After an elapse of 10 minutes, the needle-shaped material heater 115 was stopped, and separated from the needle-shaped material 109, and the needle-shaped material 109 was rapidly cooled to the temperature of −120° C. in 10 seconds by the cold finger 119 connected to the liquid nitrogen container 120.

In this low-temperature state, the deutrium gas within the gas charge container 103 was evacuated to $1 \times 10^{-7}$ Torr ($1.3 \times 10^{-5}$ Pa), the valve 105 between the analysis container 101 and the gas charge container 103 was opened, and the needle-shaped material 109 was transferred into the gas analysis container 101 by the transfer rod 111. The time required for transfer after the end of charge took was within 1 minute. The temperature of the needle-shaped material 109 during transfer was maintained at −100° C. or lower. Since an analysis position within the analysis container 101 was kept at −220° C. by the refrigerator 121 in advance, the temperature of the needle-shaped material 109 reached −220° C. in 3 minutes. A high voltage was applied to the needle-shaped material 109 so as to cause field evaporation on the tip surface of the needle-shaped material 109, and the atom probe measurement was performed using the same measuring device as the measuring device shown in FIG. 1. Measuring conditions are a pulse fraction of 20%, an applied voltage of DC 7 kV to 10 kV, and a pulse voltage of 1.4 kV to 2.0 kV. Measurement data was analyzed by POSAP software, and a mass-to-charge ratio spectrum was obtained. Hydrogen ions ($H^+$) by the ionization of remaining hydrogens within the analysis container 101 appeared as the peak of a mass-to-charge ratio of 1, whereas the peak of the charged deutrium as the deutrium ions ($D^+$) appeared in a mass-to-charge ratio of 2. As a result of drawing a three-dimensional element map on the basis of this, the deutrium charged near the interface of a minute precipitate was concentrated, and the deutrium concentration was higher than that of Example 3. This shows that, since the transfer time of the needle-shaped material 109 was shorter than that of Example 3, the escape of deutrium was further suppressed. Hence, the hydrogen existence position of the deutrium charged into the needle-shaped material could be visualized and observed with a spatial resolution at an atomic level by the present invention.

Although the preferred embodiments of the present invention have been described with reference to the accompanying drawings, it is needless to say that the present invention is not limited only to such embodiments. It will be obvious to those skilled in the art that various alternations or modifications can be made in the category as set forth in the claims, and it will be understood that these alternations or modifications naturally belong to the technical scope of the present invention.

According to the present invention, the deutrium can be simply and certainly charged into a material, and the atom probe measurement can be rapidly performed while suppressing the diffusion of the deutrium into the material. Therefore, functional improvements of the atom probe apparatus which can investigate a material from the composition of elements can be realized, and the hydrogen existence position in materials including steel materials can be made clear. Hence, the apparatus and method which greatly contribute to development of materials of which the reliability is secured can be provided.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A gas charge container comprising:
a sample holder which holds a needle-shaped material;
a deutrium gas supply portion which charges a deutrium gas into the needle-shaped material held by the sample holder; and
a heating portion which heats the needle-shaped material held by the sample holder,
wherein the needle-shaped material is cooled by blocking a heat generated by the heating portion after the needle-shaped material is heated by the heating portion.

2. The gas charge container according to claim 1,
wherein the needle-shaped material is cooled by keeping away the heating portion from the sample holder after the needle-shaped material is heated by the heating portion.

3. The gas charge container according to claim 1,
wherein the heating portion is an optical heating portion, and the needle-shaped material is cooled by stopping the optical heating portion after the needle-shaped material is heated by the optical heating portion.

4. The gas charge container according to claim 1,
wherein the needle-shaped material held by the sample holder is cooled to −50° C. or lower within 10 seconds from a temperature after the heating by the heating portion.

5. An atom probe apparatus comprising:
the gas charge container according to claim 1;
an analysis container which performs atom probe measurement of the needle-shaped material held by the sample holder; and
a conveyance portion which conveys the sample holder from the gas charge container to an analysis position within the analysis container.

6. An atom probe apparatus comprising:
the gas charge container according to claim 1;
an analysis container which performs atom probe measurement of the needle-shaped material held by the sample holder; and
a valve which connects the gas charge container and the analysis container together.

7. A method for analyzing a hydrogen position in a material using an atom probe apparatus, the method comprising the steps of:
cooling the sample holder holding the needle-shaped material as the sample to −100° C. or lower in an atmosphere including the deutrium gas supplied from the deutrium gas supply portion within the gas charge container according to claim 1;
heating the needle-shaped material to a temperature of 100° C. or higher and maintaining the needle-shaped material at the temperature by the heating portion;
cooling the needle-shaped material to −50° C. or lower within 10 seconds by the cooling portion;

conveying the sample holder in a vacuum atmosphere from an inside of the gas charge container to the analysis container using the conveyance portion in a state where the needle-shaped material is kept at −50° C. or lower after the inside of the gas charge container is evacuated, and installing the sample holder at an analysis position within the analysis container; and performing atom probe measurement of a deutrium in the needle-shaped material.

* * * * *